United States Patent
Lightner et al.

(10) Patent No.: US 7,705,204 B2
(45) Date of Patent: Apr. 27, 2010

(54) GENERATION OF PLANTS WITH ALTERED OIL CONTENT

(75) Inventors: Jonathan Lightner, Johnston, IA (US); Stephanie K. Clendennen, Kingsport, TN (US); Jeremy E. Coate, Cortland, NY (US); Nancy Anne Federspiel, Menlo Park, CA (US)

(73) Assignee: Agrigenetics Inc., Indianapolis, ID (US)

( * ) Notice: Subject to any disclaimer, the term of this patent is extended or adjusted under 35 U.S.C. 154(b) by 498 days.

(21) Appl. No.: 10/539,215

(22) PCT Filed: Dec. 18, 2003

(86) PCT No.: PCT/US03/40988

§ 371 (c)(1), (2), (4) Date: Jan. 17, 2006

(87) PCT Pub. No.: WO2004/056968

PCT Pub. Date: Jul. 8, 2004

(65) Prior Publication Data

US 2006/0174375 A1 Aug. 3, 2006

Related U.S. Application Data

(60) Provisional application No. 60/434,601, filed on Dec. 18, 2002.

(51) Int. Cl.
 *A01H 5/00* (2006.01)
 *C12N 15/82* (2006.01)
(52) U.S. Cl. .................................. 800/298; 800/281
(58) Field of Classification Search .................. None
 See application file for complete search history.

(56) References Cited

U.S. PATENT DOCUMENTS

| | | | |
|---|---|---|---|
| 5,639,790 | A | 6/1997 | Voelker et al. |
| 5,704,160 | A | 1/1998 | Bergquist et al. |
| 6,229,033 | B1 | 5/2001 | Knowlton |
| 6,248,939 | B1 | 6/2001 | Leto et al. |
| 2002/0078475 | A1 | 6/2002 | Li et al. |
| 2002/0160378 | A1 | 10/2002 | Harper et al. |

FOREIGN PATENT DOCUMENTS

| | | |
|---|---|---|
| WO | WO 01/83697 | 11/2001 |
| WO | WO 02/04648 | 1/2002 |
| WO | WO 02/10210 | 2/2002 |

OTHER PUBLICATIONS

Anoop et al., "Modulation of citrate metabolism alters aluminum tolerance in yeast and transgenic canola overexpressing a mitochondrial citrate synthase," *Plant Physiol.*, 132:2205-2217, 2003.

Beisson et al., "*Arabidopsis* genes involved in acyl lipid metabolism. A 2003 census of the candidates, a study of the distribution of expressed sequence tags in organs, and a web-based database," *Plant Physiol.*, 132:681-697, 2003.

Bert et al., "Comparative genetic analysis of quantitative traits in sunflower (*Helianthus annuus* L.). 2. Characterisation of QTL involved in developmental and agronomic traits," *Theor. Appl. Genet.*, 107:181-189, 2003.

Colbert et al., "High-throughput screening for induced point mutations," *Plant Physiol.*, 126(2):480-484, 2001.

Dehesh et al., "Overexpression of 3-ketoacyl-acyl-carrier protein synthase IIIs in plants reduces the rate of lipid synthesis," *Plant Physiol.*, 125:1103-1114, 2001.

Eccleston and Ohlrogge, "Expressions of lauroyl-acyl carrier protein thioesterase in *brassica napus* seeds induces pathways for both fatty acid oxidation and biosynthesis and implies a set point for triacylglycerol accumulation," *Plant Cell.* 10:613-621, 1998.

Fatland et al., "Molecular biology of cytosolic acetyl-CoA generation," *Biochem. Soc. Trans.*, 28(6):593-595, 2000.

Fatland et al., "Reverse genetic characterization of cytosolic acetyl-CoA generation by ATP-citrate lyase in *Arabidopsis*," *Plant Cell*, 17:182-203, 2005.

Feldmann et al., "A Dwarf Mutant of *Arabidopsis* Generated by T-DNA Insertion Mutagenesis," *Science*, 243(4896):1351-1354, 1989.

Focks and Benning, "*wrinkled1*: A novel, low-seed-oil mutant of *Arabidopsis* with a deficiency in the seed-specific regulation of carbohydrate metabolism," *Plant Physiol.*, 118:91-101, 1998.

Girke et al., "Microarray analysis of developing *Arabidopsis* seeds," *Plant Physiol.*, 124:1570-1581, 2000.

Jako et al., "Seed-specific over-expression of an *Arabidopsis* cDNA encoding a diacylglycerol acyltransferase enhances seed oil content and seed weight," *Plant Physiol.*, 126(2):861-874, 2001.

James and Dooner, "Isolation of EMS-induced mutants in *Arabidopsis* altered in seed fatty acid composition," *Theor. Appl. Genet.*, 80(2):241-245, 1990.

Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409, 1995.

Katavic et al., "Utility of the *Arabidopsis FAE1* and yeast *SLC1-1* genes for improvements in erucic acid and oil content in rapeseed," *Biochem Soc. Trans.*, 28(6):935-937, 2000.

Larson et al., "Acyl CoA profiles of transgenic plants that accumulate medium-chain fatty acids indicate inefficient storage lipid synthesis in developing oilseeds," *Plant J.*, 32:519-527, 2002.

Lemieux et al., "Mutants of *Arabidopsis* with alterations in seed lipid fatty acid composition," *Theor. Appl. Genet.*, 80(2):234-240, 1990.

(Continued)

*Primary Examiner*—Elizabeth F McElwain
(74) *Attorney, Agent, or Firm*—Donald R. Stuart; Klarquist Sparkman LLP

(57) ABSTRACT

The present invention is directed to plants that display an altered oil content phenotype due to altered expression of a citrate synthase nucleic acid. The invention is further directed to methods of generating plants with an altered oil content phenotype.

8 Claims, No Drawings

OTHER PUBLICATIONS

Lin et al., "The Pex16p homolog SSE1 and storage organelle formation in *Arabidopsis* seeds," *Science*. 284:328-330, 1999.

Lionneton et al., "Development of an AFLP-based linkage map and localization of QTLs for seed fatty acid content in condiment mustard (*Brassica juncea*)," *Genome*, 45(6):1203-1215, 2002.

Liu and Butow, "A transcriptional switch in the expression of yeast tricarboxylic acid cycle genes in response to a reduction or loss of respiratory function," *Mol. Cell. Biol.*, 19:6720-6728, 1999.

McCallum et al., "Targeted screening for induced mutations," *Nat. Biotechnol.*, 18(4):455-457, 2000.

Mekhedov et al., "Toward a functional catalog of the plant genome. A survey of genes for lipid biosynthesis," *Plant Physiol.*, 122:389-401, 2000.

Moire et al., "Impact of unusual fatty acid synthesis on futile cycling through β-oxidation and on gene expression in transgenic plants," *Plant Physiol.*, 134:432-442, 2004.

Neuhaus and Emes, "Nonphotosynthetic Metabolism in Plastids," *Annu. Rev. Plant Physiol. Plant Mol. Biol.*, 51:111-140, 2000.

O'Hara et al., "Fatty acid and lipid biosynthetic genes are expressed at constant molar ratios but different absolute levels during embryogenesis," *Plant Physiol.*, 129:310-320, 2002.

Okuley et al., "*Arabidopsis* FAD2 Gene Encodes the Enzyme That Is Essential for Polyunsaturated Lipid Synthesis," *Plant Cell*, 6:147-158, 1994.

Pritchard et al., "Germination and storage reserve mobilization are regulated independently in *Arabidopsis*," *Plant J.*, 31(5):639-647, 2002.

Rangasamy and Ratledge, "Compartmentation of ATP:Citrate lyase in plants," *Plant Physiol.*, 122:1225-1230, 2000.

Rangasamy and Ratledge, "Genetic enhancement of fatty acid synthesis by targeting rat liver ATP:citrate lyase into plastids of tobacco," *Plant Physiol.*, 122:1231-1238, 2000.

Ratledge et al, "Correlation of ATP/citrate lyase activity with lipid accumulation in developing seeds of *Brassica napus* L.," *Lipids*, 32(1):7-12, 1997.

Rawsthorne, S., "Carbon flux and fatty acid synthesis in plants," *Prog Lipid Res.*, 41:182-196, 2002.

Ruuska et al., "Contrapuntal networks of gene expression during *Arabidopsis* seed filling," *Plant Cell*, 14:1191-1206, 2002.

Rylott et al., "Co-ordinate regulation of genes involved in storage lipid mobilization in *Arabidopsis thaliana*," *Biochem Soc. Trans.*, 29:283-287, 2001.

Schnarrenberger and Martin, "Evolution of the enzymes of the citric acid cycle and the glyoxylate cycle of higher plants, A case study of endosymbiotic gene transfer," *Eur. J Biochem.*, 269:868-883, 2002.

Schnurr et al., "Characterization of an acyl-CoA synthetase from *Arabidopsis thaliana*," *Biochem Soc. Trans.*, 28(6):957-958, 2000.

Shockey et al., "Characterization of the AMP-binding protein gene family in *Arabidopsis thaliana*: will the real acyl-CoA synthetases please stand up?" *Biochem Soc. Trans.*, 28(6):955-957, 2000.

Thelen et al., "Biotin carboxyl carrier protein isoforms in Brassicaceae oilseeds," *Biochem. Soc. Trans.*, 28(6):595-598, 2000.

Wada et al., "Role of a positive regulator of root hair development, Caprice, in *Arabidopsis* root epidermal cell differentiation," *Development*, 129(23):5409-5419, 2002.

White et al., "A new set of *Arabidopsis* expressed sequence tags from developing seeds. The metabolic pathway from carbohydrates to seed oil," *Plant Physiol.*, 124:1582-1594, 2000.

Yadav et al., "Cloning of higher plant omega-3 fatty acid desaturases," *Plant Physiol.*, 103(2):467-476, 1993.

Eastmond and Graham et al., "Re-examining the role of the glyoxylate cycle in oilseeds," *Trends in Plant Science*, 6(2):72-77, 2001.

Murphy, Denis J., "The Future of New and Genetically Modified Oil Crops," J. Janick (ed.), ASHS Press, Alexandria, VA, pp. 216-219, 1999.

EBI accession No. EPOP:AX373289, Database accession No. AX373289, Mar. 1, 2002.

Database, EPO Proteins [Online] Mar. 1, 2002, "Sequence 1937 from Patent WO0210210." XP002376094 retrieved from EBI accession No. EPOP:AX373289 Database accession No. AX373289.

SEQUENCE LISTING

```
<160> NUMBER OF SEQ ID NOS: 2

<210> SEQ ID NO 1
<211> LENGTH: 1545
<212> TYPE: DNA
<213> ORGANISM: Arabidopsis thaliana

<400> SEQUENCE: 1
atggagattt cgcagagagt gaaagctaga ttagccgttc tcaccgcgca tttggcggtg      60
tctgataccg tcggattgga acaggtgttg ccggcgatcg cgccatggtg tacatcggct     120
cacattaccg ctgcacctca tggatcactc aaaggaaact tgacgatcgt cgatgagcgt     180
acggggaaga aatatcaggt ccctgtctca gagcatggta ccgttaaagc cgttgatctc     240
aagaagataa cgacggggaa ggatgataag gggctgaagt tgtacgatcc tggttacttg     300
aacacggctc cggttcgatc ttcgatttgt tacatcgacg gagatgaagg aatcttacgt     360
tatcggggat acccaattga agagttggct gagagcagta cttttattga ggttgcttat     420
ctcctcatgt atggaaatct gccttctcaa agtcagctag ctgattggga gttcactgtt     480
tctcagcatt cagctgtgcc acaaggagta ttggatatca tacagtccat gcctcatgat     540
gcacacccaa tgggagttct tgtgagtgcc atgagtgcac tttctatctt tcaccctgat     600
gcaaatcctg ctcttagtgg ccaagacatt tacaagtcaa aacaagttcg tgataaacag     660
```

-continued

```
attgttcgca ttctcggaaa ggcaccaaca attgcagcag ctgcttattt gaggacggca    720
ggcaggcctc ctgttcttcc ttcggccaac ctttcttatt cagagaattt cctctatatg    780
ctggattcaa tgggcaatag gtcttacaag cctaatcctc gtttggctcg agtgctggac    840
atcctcttca tactgcatgc tgaacatgaa atgaactgct ctactgctgc tgctcggcat    900
cttgcctcta gtggtgttga tgtgtacacc gcatgtgctg gagctgttgg ggcgctttat    960
ggtccacttc atggtggcgc gaacgaggcc gtgcttaaga tgttagcaga gattgggact   1020
gctgaaaata ttccagattt cattgaaggc gtgaagaaca gaaagaggaa gatgtcaggt   1080
tttggacatc gtgtttacaa aaactatgac ccccgagcaa aagttataaa aaaactggca   1140
gatgaagtgt tctccattgt tggtagggat cctctcatcg aggtagcagt tgctctagag   1200
aaggcggcac tgtctgatga atattttgtt aagagaaagc tgtacccaaa tgttgatttc   1260
tactctggat taatctatag ggcaatggga ttcccaccag aattcttcac agtcctgttc   1320
gcagtcccgc gtatggctgg atacttgtca cactggcgtg agtcgttaga tgatcctgac   1380
actaggatca tgagacccca acaggcctat actggagtgt ggatgaggca ttacgagcca   1440
gtgagagaac gaacgttatc aagtgattcg gataaggata agtttggtca agtttccatt   1500
tcgaatgcat caagaaggcg tttagctgga tcatctgccc tttag                   1545
```

```
<210> SEQ ID NO 2
<211> LENGTH: 514
<212> TYPE: PRT
<213> ORGANISM: Arabidopsis thaliana

<400> SEQUENCE: 2

Met Glu Ile Ser Gln Arg Val Lys Ala Arg Leu Ala Val Leu Thr Ala
1               5                   10                  15

His Leu Ala Val Ser Asp Thr Val Gly Leu Glu Gln Val Leu Pro Ala
            20                  25                  30

Ile Ala Pro Trp Cys Thr Ser His Ile Thr Ala Ala Pro His Gly
        35                  40                  45

Ser Leu Lys Gly Asn Leu Thr Ile Val Asp Glu Arg Thr Gly Lys Lys
    50                  55                  60

Tyr Gln Val Pro Val Ser Glu His Gly Thr Val Lys Ala Val Asp Leu
65                  70                  75                  80

Lys Lys Ile Thr Thr Gly Lys Asp Asp Lys Gly Leu Lys Leu Tyr Asp
                85                  90                  95

Pro Gly Tyr Leu Asn Thr Ala Pro Val Arg Ser Ile Cys Tyr Ile
            100                 105                 110

Asp Gly Asp Glu Gly Ile Leu Arg Tyr Arg Gly Tyr Pro Ile Glu Glu
        115                 120                 125

Leu Ala Glu Ser Ser Thr Phe Ile Glu Val Ala Tyr Leu Leu Met Tyr
    130                 135                 140

Gly Asn Leu Pro Ser Gln Ser Gln Leu Ala Asp Trp Glu Phe Thr Val
145                 150                 155                 160

Ser Gln His Ser Ala Val Pro Gln Gly Val Leu Asp Ile Ile Gln Ser
                165                 170                 175

Met Pro His Asp Ala His Pro Met Gly Val Leu Val Ser Ala Met Ser
            180                 185                 190

Ala Leu Ser Ile Phe His Pro Asp Ala Asn Pro Ala Leu Ser Gly Gln
        195                 200                 205

Asp Ile Tyr Lys Ser Lys Gln Val Arg Asp Lys Gln Ile Val Arg Ile
    210                 215                 220
```

-continued

```
Leu Gly Lys Ala Pro Thr Ile Ala Ala Ala Tyr Leu Arg Thr Ala
225                 230             235             240

Gly Arg Pro Pro Val Leu Pro Ser Ala Asn Leu Ser Tyr Ser Glu Asn
                245             250             255

Phe Leu Tyr Met Leu Asp Ser Met Gly Asn Arg Ser Tyr Lys Pro Asn
            260             265             270

Pro Arg Leu Ala Arg Val Leu Asp Ile Leu Phe Ile Leu His Ala Glu
        275             280             285

His Glu Met Asn Cys Ser Thr Ala Ala Ala Arg His Leu Ala Ser Ser
    290             295             300

Gly Val Asp Val Tyr Thr Ala Cys Ala Gly Ala Val Gly Ala Leu Tyr
305             310             315             320

Gly Pro Leu His Gly Gly Ala Asn Glu Ala Val Leu Lys Met Leu Ala
            325             330             335

Glu Ile Gly Thr Ala Glu Asn Ile Pro Asp Phe Ile Glu Gly Val Lys
            340             345             350

Asn Arg Lys Arg Lys Met Ser Gly Phe Gly His Arg Val Tyr Lys Asn
        355             360             365

Tyr Asp Pro Arg Ala Lys Val Ile Lys Lys Leu Ala Asp Glu Val Phe
    370             375             380

Ser Ile Val Gly Arg Asp Pro Leu Ile Glu Val Ala Val Ala Leu Glu
385             390             395             400

Lys Ala Ala Leu Ser Asp Glu Tyr Phe Val Lys Arg Lys Leu Tyr Pro
            405             410             415

Asn Val Asp Phe Tyr Ser Gly Leu Ile Tyr Arg Ala Met Gly Phe Pro
            420             425             430

Pro Glu Phe Phe Thr Val Leu Phe Ala Val Pro Arg Met Ala Gly Tyr
        435             440             445

Leu Ser His Trp Arg Glu Ser Leu Asp Asp Pro Asp Thr Arg Ile Met
        450             455             460

Arg Pro Gln Gln Ala Tyr Thr Gly Val Trp Met Arg His Tyr Glu Pro
465             470             475             480

Val Arg Glu Arg Thr Leu Ser Ser Asp Ser Asp Lys Asp Lys Phe Gly
            485             490             495

Gln Val Ser Ile Ser Asn Ala Ser Arg Arg Arg Leu Ala Gly Ser Ser
            500             505             510

Ala Leu
```

GENERATION OF PLANTS WITH ALTERED OIL CONTENT

REFERENCE TO RELATED APPLICATIONS

This is the §371 U.S. National Stage of International Application No. PCT/US2003/040988, filed on Dec. 18, 2003, which was published in English under PCT Article 21(2), and which in turn the benefit of U.S. provisional patent application No. 60/434,601 filed Dec. 18, 2002, both of which are hereby incorporated by reference.

BACKGROUND OF THE INVENTION

The ability to manipulate the composition of crop seeds, particularly the content and composition of seed oils, has important applications in the agricultural industries, relating both to processed food oils and to oils for animal feeding. Seeds of agricultural crops contain a variety of valuable constituents, including oil, protein and starch. Industrial processing can separate some or all of these constituents for individual sale in specific applications. For instance, nearly 60% of the US soybean crop is crushed by the soy processing industry. Soy processing yields purified oil, which is sold at high value, while the remainder is sold principally for lower value livestock feed (US Soybean Board, 2001 Soy Stats). Canola seed is crushed to produce oil and the co-product canola meal (Canola Council of Canada). Nearly 20% of the 1999/2000 US corn crop was industrially refined, primarily for production of starch, ethanol and oil (Corn Refiners Association). Thus, it is often desirable to maximize oil content of seeds. For instance, for processed oilseeds such as soy and canola, increasing the absolute oil content of the seed will increase the value of such grains. For processed corn it may be desired to either increase or decrease oil content, depending on utilization of other major constituents. Decreasing oil may improve the quality of isolated starch by reducing undesired flavors associated with oil oxidation. Alternatively, in ethanol production, where flavor is unimportant, increasing oil content may increase overall value. In many fed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors.

Biotechnological manipulation of oils can provide compositional alteration and improvement of oil yield. Compositional alterations include high oleic soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from ~3.5% to ~7%, improving the energy content of the grain.

While it has been fruitful, the HOC production system has inherent limitations. First, the system of having a low percentage of pollinators responsible for an entire field's seed set contains inherent risks, particularly in drought years. Second, oil contents in current HOC fields have plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

The most obvious target crops for the processed oil market are soy and rapeseed, and a large body of commercial work (e.g., U.S. Pat. No. 5,952,544; PCT application WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux B, et al. 1990, Theor Appl Genet 80, 234-240; James D W and Dooner H K (1990) Theor Appl Genet 80, 241-245). T-DNA mutagenesis screens (Feldmann et al., Science 243: 1351-1354, 1989) that detected altered fatty acid composition identified the omega 3 desaturase (FAD3) and delta-12 desaturase (FAD2) genes (U.S. Pat. No. 5,952,544; Yadav N S et al. (1993) Plant Physiol 103, 467-476; Okuley et al., Plant Cell. 1994 January; 6(1):147-58). A screen which focused on oil content rather than oil quality, analyzed chemically-induced mutants for wrinkled seeds or altered seed density, from which altered seed oil content was inferred (Focks N and Benning C, Plant Physiol 118:91-101, 1998). Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al, Plant Physiol. 1995 May; 108(1):399-409). It was further shown that seed-specific over-expression of the DGAT cDNA was associated with increased seed oil content (Jako et al., Plant Physiol. 2001 June; 126(2):861-74).

SUMMARY OF THE INVENTION

The invention provides a transgenic plant having a high oil phenotype. The transgenic plant comprises a transformation vector comprising a nucleotide sequence that encodes or is complementary to a sequence that encodes a citrate synthase polypeptide. In preferred embodiments, the transgenic plant is selected from the group consisting of rapeseed, soy, corn, sunflower, cotton, cocoa, safflower, oil palm, coconut palm, flax, castor and peanut. The invention further provides a method of producing oil comprising growing the transgenic plant and recovering oil from said plant.

The transgenic plant of the invention is produced by a method that comprises introducing into progenitor cells of the plant a plant transformation vector comprising a nucleotide sequence that encodes or is complementary to a sequence that encodes a citrate synthase polypeptide, and growing the transformed progenitor cells to produce a transgenic plant, wherein the citrate synthase polynucleotide sequence is expressed causing the high oil phenotype.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al. Molecular Cloning: A Laboratory Manual (Second Edition), Cold Spring Harbor Press, Plainview, N.Y., 1989, and Ausubel F M et al. Current Protocols in Molecular Biology, John Wiley & Sons, New York, N.Y., 1993, for definitions and terms of the art. It is to be understood that this invention is not limited to the particular methodology, protocols, and reagents described, as these may vary.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, progagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "altered oil content phenotype" refers to measurable phenotype of a genetically modified plant, where the plant displays a statistically significant increase or decrease in overall oil content (i.e., the percentage of seed mass that is oil), as compared to the similar, but non-modified plant. A high oil phenotype refers to an increase in overall oil content.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Identification of Plants with an Altered Oil Content Phenotype

Transgenic plants were produced to over-express various genes encoding enzymes of the glyoxylate pathway and seed from the T1 transgenic plants were tested for a high oil phenotype. It was discovered that overexpression of citrate synthase (At3g58750; GI#15231130) confers an altered oil content phenotype (specifically, a high seed oil phenotype). Accordingly, citrate synthase genes and/or polypeptides may be employed in the development of genetically modified plants having a modified oil content phenotype. Citrate synthase genes may be used in the generation of oilseed crops that provide improved oil yield from oilseed processing and in the generation of feed grain crops that provide increased energy for animal feeding. Citrate synthase genes may further be used to increase the oil content of specialty oil crops, in order to augment yield of desired unusual fatty acids. Transgenic plants that have been genetically modified to express citrate synthase can be used in the production of oil, wherein the transgenic plants are grown, and oil is obtained from plant parts (e.g. seed) using standard methods.

Citrate Synthase Nucleic Acids and Polypeptides

*Arabidopsis* citrate synthase nucleic acid is provided in SEQ ID NO:1 and in Genbank entry GI#30694870. The corresponding protein sequence is provided in SEQ ID NO:2 and in GI#15231130. Nucleic acids and/or proteins that are orthologs or paralogs of *Arabidopsis* citrate synthase, are described in Example 2 below.

As used herein, the term "citrate synthase polypeptide" refers to a full-length citrate synthase protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active citrate synthase polypeptide causes an altered oil content phenotype when mis-expressed in a plant. In a further preferred embodiment, mis-expression of the citrate synthase polypeptide causes a high oil phenotype in a plant. In another embodiment, a functionally active citrate synthase polypeptide is capable of rescuing defective (including deficient) endogenous citrate synthase activity when expressed in a plant or in plant cells; the rescuing polypeptide may be from the same or from a different species as that with defective activity. In another embodiment, a functionally active fragment of a full length citrate synthase polypeptide (i.e., a native polypeptide having the sequence of SEQ ID NO:2 or a naturally occurring ortholog thereof) retains one of more of the biological properties associated with the full-length citrate synthase polypeptide, such as catalytic activity. A citrate synthase fragment preferably comprises a citrate synthase domain, such as a C- or N-terminal or catalytic domain, among others, and preferably comprises at least 10, preferably at least 20, more preferably at least 25, and most preferably at least 50 contiguous amino acids of a citrate synthase protein. Functional domains can be identified using the PFAM program (Bateman A et al., 1999 Nucleic Acids Res 27:260-262; website at pfam.wustl.edu). Functionally active variants of full-length citrate synthase polypeptides or fragments thereof include polypeptides with amino acid insertions, deletions, or substitutions that retain one of more of the biological properties associated with the full-length citrate synthase polypeptide.

In some cases, variants are generated that change the post-translational processing of a citrate synthase polypeptide. For instance, variants may have altered protein transport or protein localization characteristics or altered protein half-life compared to the native polypeptide.

As used herein, the term "citrate synthase nucleic acid" encompasses nucleic acids with the sequence provided in or complementary to the sequence provided in SEQ ID NO:1, as well as functionally active fragments, derivatives, or orthologs thereof. A citrate synthase nucleic acid of this invention may be DNA, derived from genomic DNA or cDNA, or RNA.

In one embodiment, a functionally active citrate synthase nucleic acid encodes or is complementary to a nucleic acid that encodes a functionally active citrate synthase polypeptide. Included within this definition is genomic DNA that serves as a template for a primary RNA transcript (i.e., an mRNA precursor) that requires processing, such as splicing, before encoding the functionally active citrate synthase polypeptide. A citrate synthase nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed citrate synthase polypeptide, or an intermediate form. A citrate synthase polynucleotide can also include heterologous coding sequences, for example, sequences that encode a marker included to facilitate the purification of the fused polypeptide, or a transformation marker.

In another embodiment, a functionally active citrate synthase nucleic acid is capable of being used in the generation of loss-of-function citrate synthase phenotypes, for instance, via antisense suppression, co-suppression, etc.

In one preferred embodiment, a citrate synthase nucleic acid used in the methods of this invention comprises a nucleic acid sequence that encodes or is complementary to a sequence that encodes a citrate synthase polypeptide having at least 50%, 60%, 70%, 75%, 80%, 85%, 90%, 95% or more sequence identity to the polypeptide sequence presented in SEQ ID NO:2.

In another embodiment a citrate synthase polypeptide of the invention comprises a polypeptide sequence with at least 50% or 60% identity to the citrate synthase polypeptide sequence of SEQ ID NO:2, and may have at least 70%, 80%, 85%, 90% or 95% or more sequence identity to the citrate synthase polypeptide sequence of SEQ ID NO:2. In another embodiment, a citrate synthase polypeptide comprises a polypeptide sequence with at least 50%, 60%, 70%, 80%, 85%, 90% or 95% or more sequence identity to a functionally active fragment of the polypeptide presented in SEQ ID NO:2. In yet another embodiment, a citrate synthase polypeptide comprises a polypeptide sequence with at least 50%, 60%, 70%, 80%, or 90% identity to the polypeptide sequence of SEQ ID NO:2 over its entire length.

In another aspect, a citrate synthase polynucleotide sequence is at least 50% to 60% identical over its entire length to the citrate synthase nucleic acid sequence presented as SEQ ID NO:1, or nucleic acid sequences that are complementary to such a citrate synthase sequence, and may comprise at least 70%, 80%, 85%, 90% or 95% or more sequence identity to the citrate synthase sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410; website at blast.wustl.edu/blast/README.html) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the nucleic acid sequence of SEQ ID NO:1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of SEQ ID NO:1 under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a citrate synthase polypeptide can be produced. For example, codons may be selected to increase the rate at which expression of the polypeptide occurs in a particular host species, in accordance with the optimum codon usage dictated by the particular host organism (see, e.g., Nakamura et al, 1999, Nucleic Acids Res 27:292). Such sequence variants may be used in the methods of this invention.

The methods of the invention may use orthologs of the *Arabidopsis* citrate synthase. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, supra; Dieffenbach C and Dveksler G (Eds.) PCR Primer: A Laboratory Manual, Cold Spring Harbor Laboratory Press, New York, 1989). For instance, methods for generating a cDNA library from the plant species of interest and probing the library with partially homologous gene probes are described in Sambrook et al, supra. A highly conserved portion of the *Arabidopsis* citrate synthase coding sequence may be used as a probe. Citrate synthase ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known citrate synthase polypeptides are used for ortholog isolation (see, e.g., Harlow E and Lane D, Using Antibodies: A Laboratory Manual, Cold Spring Harbor Laboratory Press, 1999, New York). Western blot analysis can determine that a citrate synthase ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., supra. Once the candidate ortholog(s) are identified by any of these means, candidate orthologous sequence are used as bait (the "query") for the reverse BLAST against sequences from *Arabidopsis* or other species in which citrate synthase nucleic acid and/or polypeptide sequences have been identified.

Citrate synthase nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., *Methods Enzymol.* 204:125-39, 1991), may be used to introduce desired changes into a cloned nucleic acid.

In general, the methods of the invention involve incorporating the desired form of the citrate synthase nucleic acid into a plant expression vector for transformation of in plant cells, and the citrate synthase polypeptide is expressed in the host plant.

An isolated citrate synthase nucleic acid molecule is other than in the form or setting in which it is found in nature and is identified and separated from least one contaminant nucleic acid molecule with which it is ordinarily associated in the natural source of the citrate synthase nucleic acid. However, an isolated citrate synthase nucleic acid molecule includes citrate synthase nucleic acid molecules contained in cells that ordinarily express citrate synthase where, for example, the nucleic acid molecule is in a chromosomal location different from that of natural cells.

Generation of Genetically Modified Plants with an Altered Oil Content Phenotype

Citrate synthase nucleic acids and polypeptides may be used in the generation of genetically modified plants having a modified oil content phenotype. As used herein, a "modified oil content phenotype" may refer to modified oil content in any part of the plant; the modified oil content is often observed in seeds. In a preferred embodiment, altered expression of the citrate synthase gene in a plant is used to generate plants with a high oil phenotype.

The methods described herein are generally applicable to all plants. In a preferred embodiment, the invention is directed to oil-producing plants, which produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The invention may also be directed to fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species that may be a source of unique fatty acids.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising a citrate synthase polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.).

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as rapeseed (De Block et al., Plant Physiol. (1989) 91:694-701), sunflower (Everett et al., Bio/Technology (1987) 5:1201), and soybean (Christou et al., Proc. Natl. Acad. Sci USA (1989) 86:7500-7504; Kline et al., Nature (1987) 327:70).

Expression (including transcription and translation) of citrate synthase may be regulated with respect to the level of expression, the tissue type(s) where expression takes place and/or developmental stage of expression. A number of heterologous regulatory sequences (e.g., promoters and enhancers) are available for controlling the expression of a citrate synthase nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the 35S CaMV (Jones J D et al, Transgenic Res 1:285-297 1992), the CsVMV promoter (Verdaguer B et al., Plant Mol Biol 37:1055-1067, 1998) and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., Plant Mol Bio 21:625-640, 1993).

In one preferred embodiment, citrate synthase expression is under control of regulatory sequences from genes whose expression is associated with early seed and/or embryo development. Legume genes whose promoters are associated with early seed and embryo development include *V. faba legumin* (Baumlein et al., 1991, Mol Gen Genet 225:121-8; Baumlein et al., 1992, Plant J 2:233-9), *V. faba usp* (Fiedler et al., 1993, Plant Mol Biol 22:669-79), pea *convicilin* (Bown et al., 1988, Biochem J 251:717-26), pea *lectin* (dePater et al., 1993, Plant Cell 5:877-86), *P. vulgaris beta phaseolin* (Bustos et al., 1991, EMBO J 10:1469-79), *P. vulgaris* DLEC2 and PHS [beta] (Bobb et al, 1997, Nucleic Acids Res 25:641-7), and soybean *beta-Conglycinin,* 7S storage protein (Chamberland et al., 1992, Plant Mol Biol 19:937-49). Cereal genes whose promoters are associated with early seed and embryo development include rice *glutelin* ("GluA-3," Yoshihara and Takaiwa, 1996, Plant Cell Physiol 37:107-11; "GluB-1," Takaiwa et al., 1996, Plant Mol Biol 30:1207-21; Washida et al., 1999, Plant Mol Biol 40:1-12; "Gt3," Leisy et al., 1990, Plant Mol Biol 14:41-50), rice *prolamin* (Zhou & Fan, 1993, Transgenic Res 2:141-6), wheat *prolamin* (Hammond-Kosack et al., 1993, EMBO J 12:545-54), *maize zein* (Z4, Matzke et al., 1990, Plant Mol Biol 14:323-32), and barley *B-hordeins* (Entwistle et al., 1991, Plant Mol Biol 17:1217-31). Other genes whose promoters are associated with early seed and embryo development include oil palm GLO7A (7S globulin, Morcillo et al., 2001, Physiol Plant 112:233-243), *Brassica napus napin,* 2S storage protein, and napA gene (Josefsson et al., 1987, J Biol Chem 262:12196-201; Stalberg et al., 1993, Plant Mol Biol 1993 23:671-83; Ellerstrom et al., 1996, Plant Mol Biol 32:1019-27), *Brassica napus oleosin* (Keddie et al., 1994, Plant Mol Biol 24:327-40), *Arabidopsis oleosin* (Plant et al., 1994, Plant Mol Biol 25:193-205), *Arabidopsis* FAE1 (Rossak et al., 2001, Plant Mol Biol 46:717-25), *Canavalia gladiata* conA (Yamamoto et al., 1995, Plant Mol Biol 27:729-41), and *Catharaithus roseus* strictosidine synthase (Str, Ouwerkerk and Memelink, 1999, Mol Gen Genet 261:635-43). In another preferred embodiment, regulatory sequences from genes expressed during oil biosynthesis are used (see, e.g., U.S. Pat. No. 5,952,544). Alternative promoters are from plant storage protein genes (Bevan et al, 1993, Philos Trans R Soc Lond B Biol Sci 342:209-15).

In yet another aspect, in some cases it may be desirable to inhibit the expression of endogenous citrate synthase in a host cell. Exemplary methods for practicing this aspect of the invention include, but are not limited to antisense suppression (Smith, et al., *Nature* 334:724-726, 1988; van der Krol et al., Biotechniques (1988) 6:958-976); co-suppression (Napoli, et al, *Plant Cell* 2:279-289, 1990); ribozymes (PCT Publication WO 97/10328); and combinations of sense and antisense (Waterhouse, et al., *Proc. Natl. Acad. Sci. USA* 95:13959-13964, 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., Proc. Natl. Acad. Sci. USA (1988) 85:8805-8809), a partial cDNA sequence including fragments of 5' coding sequence, (Cannon et al., Plant Molec. Biol. (1990) 15:39-47), or 3' non-coding sequences (Ch'ng et al., Proc. Natl. Acad. Sci. USA (1989) 86:10006-10010). Cosuppression techniques may use the entire cDNA sequence (Napoli et al., supra; van der Krol et al., The Plant Cell (1990) 2:291-299) or a partial cDNA sequence (Smith et al., Mol. Gen. Genetics (1990) 224:477-481).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, *Arch Virol Suppl* 15:189-201, 1999]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., *Cur Opin Plant Biol.* 2(2):96-103, 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Oil Content Phenotype

The invention further provides a method of identifying plants that have mutations in endogenous citrate synthase that confer altered oil content, and generating altered oil content progeny of these plants that are not genetically modified. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. Citrate synthase-specific PCR is used to identify whether a mutated plant has a citrate synthase mutation. Plants having citrate synthase mutations may then be tested for altered oil content, or alternatively, plants may be tested for altered oil content, and then citrate synthase-specific PCR is used to determine whether a plant having altered oil content has a mutated citrate synthase gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

In another method, a candidate gene/Quantitative Trait Locus (QTLs) approach can be used in a marker-assisted breeding program to identify alleles of or mutations in the citrate synthase gene or orthologs of citrate synthase that may confer altered oil content (see Bert et al., Theor Appl Genet.

2003 June; 107(1):181-9; and Lionneton et al, Genome. 2002 December; 45(6): 1203-15). Thus, in a further aspect of the invention, a citrate synthase nucleic acid is used to identify whether a plant having altered oil content has a mutation in endogenous citrate synthase or has a particular allele that causes altered oil content.

All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Generation of Transgenic Plants Overexpressing Citrate Synthase

A subset of the genes encoding enzymes of the glyoxylate pathway were over-expressed in wild-type *Arabidopsis* and seed from the T1 transgenic plants were tested for a high oil phenotype. To over-express the genes, genomic DNA was PCR amplified with primers specific for each gene. The PCR product was cloned behind the CsVMV promoter in a T-DNA vector containing the NPTII gene (which serves as a selectable marker) and transformed into wild-type *Arabidopsis* plants. Transgenic plants were selected by germinating seeds on agar medium containing kanamycin. Kanamycin resistant seedlings were transplanted to soil and grown to maturity. Non-transformed wild-type Col-0 plants were used as a control. Seed was germinated on agar medium (lacking kanamycin) and seedlings were transplanted to soil and grown to maturity. Oil content in seed harvested from both the transgenic and control plants was measured using Near Infrared Spectroscopy (NIR). NIR infrared spectra were captured using a Bruker 22 N/F. Bruker Software was used to estimate total seed oil content using data from NIR analysis and reference methods according to the manufacturers instructions.

The results showed that over-expression of the *Arabidopsis* citrate synthase gene (At3g58750) confers a high seed oil phenotype. Seed from 4 transgenic lines over-expressing At3g58750 (encoding citrate synthase) had more oil than all of the control plants tested. The values ranged from 41.6% to 41.2% oil for the transgenic plants while the values from the control seed ranged between 40.9% and 38.7%. The average oil content in the control seed was 39.9%. Over-expression of citrate synthase can confer as much as a 7% increase in seed oil.

Example 2

Analysis of *Arabidopsis* Citrate Synthase

Sequence analyses were performed with BLAST (Altschul et al., 1997, J. Mol. Biol. 215:403-410), PFAM (Bateman et al., 1999, Nucleic Acids Res 27:260-262), PSORT (Nakai K, and Horton P, 1999, Trends Biochem Sci 24:34-6), and/or CLUSTAL (Thompson J D et al, 1994, Nucleic Acids Res 22:4673-4680). Numerous orthologs were identified having high sequence identity, and thus are expected to also confer a high oil phenotype when overexpressed in a plant. Orthologous citrate synthases from various plant species include: GI#1345933, and GI#975633 (*Cucurbita* cv.); GI#15231128, and GI#11268305 (*Arabidopsis thaliana*); GI#8928010 (*Daucus carota*); GI#6647461 (*Solanum tuberosum*); GI#1352088 (*Citrus maxima*); GI#15982952 (*Prunus persica*); GI#11066954 (*Oryza sativa*); GI#2300712 (*Nicotiana tabacum*), and GI#2300710 (*Beta vulgaris*).

It is claimed:

1. A transgenic plant comprising a plant transformation vector comprising a nucleotide sequence that encodes a citrate synthase polypeptide having at least 95% sequence identity with SEQ ID NO:2, wherein the transgenic plant over-expresses the citrate synthase polypeptide relative to a non-transgenic control plant, and whereby the transgenic plant has a high oil phenotype relative to the control plant.

2. The transgenic plant of claim 1, which is selected from the group consisting of rapeseed, soy, corn, sunflower, cotton, cocoa, safflower, oil palm, coconut palm, flax, castor and peanut.

3. A plant part obtained from the plant according to claim 1.

4. The plant part of claim 3, which is a seed.

5. A method of producing oil comprising growing the transgenic plant of claim 1 and recovering oil from said plant.

6. A method of producing a high oil phenotype in a plant, said method comprising:
   a) introducing into progenitor cells of the plant a plant transformation vector comprising a nucleotide sequence that encodes a citrate synthase polypeptide having at least 95% sequence identity with SEQ ID NO:2, and
   b) growing the transformed progenitor cells to produce a transgenic plant, wherein said nucleotide sequence is over-expressed relative to a non-transgenic control plant, and said transgenic plant exhibits a high oil content phenotype relative to the control plant.

7. A plant obtained by the method of claim 6.

8. The plant of claim 7, which is selected from the group consisting of rapeseed, soy, corn, sunflower, cotton, cocoa, safflower, oil palm, coconut palm, flax, castor and peanut.

* * * * *

UNITED STATES PATENT AND TRADEMARK OFFICE
CERTIFICATE OF CORRECTION

| | |
|---|---|
| PATENT NO. | : 7,705,204 B2 |
| APPLICATION NO. | : 10/539215 |
| DATED | : April 27, 2010 |
| INVENTOR(S) | : Lightner et al. |

It is certified that error appears in the above-identified patent and that said Letters Patent is hereby corrected as shown below:

Column 1, line 9, "in turn the benefit" should read --in turn claims the benefit--.

Signed and Sealed this

Twelfth Day of October, 2010

David J. Kappos
*Director of the United States Patent and Trademark Office*